(12) United States Patent
Gregory et al.

(10) Patent No.: US 8,811,696 B2
(45) Date of Patent: *Aug. 19, 2014

(54) MORPHOMETRY OF THE HUMAN HIP JOINT AND PREDICTION OF OSTEOARTHRITIS

(75) Inventors: Jennifer Susan Gregory, Aberdeen (GB); Richard Malcom Aspden, Ellon (GB); Rebecca Jane Barr, Angus (GB); Kanako Yoshidashire, Aberdeen (GB); David Macaulay Reid, Aberdeen (GB)

(73) Assignees: Wyeth Pharmaceuticals, Inc., Madison, NJ (US); TMRI, Ltd (GB)

(*) Notice: Subject to any disclaimer, the term of this patent is extended or adjusted under 35 U.S.C. 154(b) by 588 days.

This patent is subject to a terminal disclaimer.

(21) Appl. No.: 13/058,619

(22) PCT Filed: Aug. 12, 2009

(86) PCT No.: PCT/GB2009/051011
§ 371 (c)(1), (2), (4) Date: Jun. 7, 2011

(87) PCT Pub. No.: WO2010/018406
PCT Pub. Date: Feb. 18, 2010

(65) Prior Publication Data
US 2011/0243416 A1    Oct. 6, 2011

(30) Foreign Application Priority Data

Aug. 12, 2008 (GB) .................................. 0814714.2
May 8, 2009 (GB) .................................. 0907933.6

(51) Int. Cl.
*G06K 9/00* (2006.01)
(52) U.S. Cl.
USPC ............................ 382/128; 382/131; 382/132

(58) Field of Classification Search
None
See application file for complete search history.

(56) References Cited

U.S. PATENT DOCUMENTS

| | | | |
|---|---|---|---|
| 5,259,384 | A | 11/1993 | Kaufman et al. |
| 5,348,009 | A | 9/1994 | Ohtomo et al. |

(Continued)

FOREIGN PATENT DOCUMENTS

| | | |
|---|---|---|
| EP | 0570936 | 9/2000 |
| WO | 94/06351 | 3/1994 |

(Continued)

OTHER PUBLICATIONS

Practical Statistics for Medical Research, pp. 1-99.

(Continued)

*Primary Examiner* — Amir Alavi
*Assistant Examiner* — Kenny Cese
(74) *Attorney, Agent, or Firm* — Renner Kenner Greive Bobak Taylor & Weber

(57) ABSTRACT

An apparatus and method for analyzing the morphometry of a human hip joint is provided. The apparatus includes image receiving means for receiving a digital image of a hip joint and image analysis means, including an Active Shape Model configured to identify a set of landmark points on the image, wherein the set of points includes points which correspond to features of the proximal femur and the region of the pelvis forming the acetabulum. The ASM is further configured to generate an image data-set from the co-ordinates of the landmark points; and data comparison means for comparing the image data-set with one or more comparative data-sets to obtain value(s) for one or more output modes which characterize the variation of the image data-set from the comparative data-set(s), to provide an indication of the presence and/or severity of osteoarthritis in the hip and/or the risk of the hip joint developing osteoarthritis.

18 Claims, 6 Drawing Sheets

(56) References Cited

U.S. PATENT DOCUMENTS

| | | | |
|---|---|---|---|
| 5,931,780 | A | 8/1999 | Giger |
| 6,038,281 | A | 3/2000 | Mazess |
| 6,213,958 | B1 | 4/2001 | Winder |
| 7,379,529 | B2 | 5/2008 | Lang |
| 7,660,453 | B2 | 2/2010 | Lang |
| 7,769,213 | B2 | 8/2010 | Gregory et al. |
| 7,929,745 | B2 | 4/2011 | Walker et al. |
| 2004/0242987 | A1 | 12/2004 | Liew et al. |
| 2005/0010106 | A1* | 1/2005 | Lang et al. ............... 600/425 |
| 2007/0249967 | A1* | 10/2007 | Buly et al. ............... 600/595 |
| 2007/0274442 | A1* | 11/2007 | Gregory et al. ............ 378/54 |
| 2009/0208081 | A1* | 8/2009 | Saha et al. ............... 382/131 |

FOREIGN PATENT DOCUMENTS

| | | |
|---|---|---|
| WO | 0138824 | 5/2001 |
| WO | 2005045730 | 5/2005 |
| WO | 2006104707 | 10/2006 |
| WO | 2007058918 | 5/2007 |

OTHER PUBLICATIONS

Practical Statistics for Medical Research, pp. 100-199.
Practical Statistics for Medical Research, pp. 200-299.
Practical Statistics for Medical Research, pp. 300-399.
Practical Statistics for Medical Research, pp. 400-499.
Practical Statistics for Medical Research, pp. 500-611.
Gregory, et al., Hip fractures, morphometry and geometry, Apr. 2002.
Testi, et al., Prediction of Hip Fracture Can Be Significantly Improved by a Single Biomedical Indicator, 2002.
J.S. Gregory, et al., "A method for assessment of the shape of the proximal femur and its relationship to osteoporotic hip fracture", International Osteoporosis Foundation and National Osteoporosis Foundation, No. 7, 2003, pp. 5-11, United Kingdom, XP-002318248.
C. Bergot et al., "Hip Fracture Risk and Proximal Femur Geometry and DXA Scans", International Osteoporosis Foundation and National Osteoporosis Foundation, 2002, pp. 542-550, United Kingdom, XP-002318249.
C.J. Taylor, "Model-based interpretation of complex and variable images", Department of Medical Biophysics, 1997, United Kingdom, XP-002318250.
J.S. Gregory et al., Analysis of Trabecular Bone Structure Using Fourier Transforms and Neural Networks:, IEEE Transaction on Information Technology in Biomedicine, vol. 3, No. 4, Dec. 1999, pp. 289-294, XP-002318251.
Sharmila Majumdar, et al., "Fractal analysis of radiographs: Assessment of trabecular bone structure and prediction of elastic modulus and strength", Magnetic Resonance Science Center and Osteopososis and Arthritis Research Group, Department of Radiology, University of California, San Francisco, California 94143, Med. Phys. 26 (7), Jul. 1999.
Slison Stewart, et al., "Bone Density and Bone Turnover in Patients with Osteoarthritis and Osteoporosis", The Journal of Rheumatology, 1999; 26:3 pp. 622-626.
Assessment of osteoporosis and osteoarthritis using active shape and active apperance models with DXA scans; Gregory J.S, Barr R.J, Stewart A, Reid D.M, Aspden R.M; Jul. 2007; Journal of Bone and Mineral Research, vol. 22, No. 7.
Fracture risk assessment model: Do values derived from Western populations apply to other Caucasians?; Arabi A, Awada H, Baddoura R, Haddad S, Khoury N.J, Ayoub G, Fuleihan G. El-hail; Sep. 2005; Journal of Bone and Mineral Research; vol. 20, No. 9, Suppl.
Femoral Fracture Risk assessment after intensity modulated radiation therapy (IMRT) for the treatment of soft tissue sarcoma using a novel mathematical model; Song Y, Wang S, Chan M, Chandra B, Dhawan A, Song Y; 2006; IEEE cat. No. 06CH37748.
Measurement of femoral Neck antevesion in 30. 2. 3D modelling method; Kim J.S, Park T.S, Park S.B, Kim J.S, Kim I.Y, Kim S.I; Nov. 2000; Medical & Biological Engineering & Computing; vol. 38 No. 6.
Automatic reconstruction of patient-spefic surface model of a proximal femur from calibrated X-ray images via Bayesian Filters; Guoyan Zheng, Xiao Dong; 2007; Advanced Intelligent Computing Theories and Applications. With Aspects of Theoretical and Methodological Issues. Proceedings Third International Conference on Intelligent Computing, ICIC; vol. 4681.
Femur bone mass distribution by DXA predicts hip fracture risk better than femur bone density; Del Rio L, Di Gergorio 5, Bagur A, et al; Jan. 2006; Calcifield Tissue International; vol. 78, Supp. 1.
DXA and active appearance modelling: A novel method for assessment of Osteoarthritis; Gregory J.S, Campbell CD, Yoshida K, et al; Jun. 2007; Bone (New York); vol. 40, No. 6 Supp 2.
Use of DXA-Based Structural engineering models of the proximal femur to predict hip fracture; Yan L, Peel N, Clowes J, McCloskey E.V, Eastell R; Sep. 2007; Journal of Bone and Mineral Research; vol. 22, supp 1.
A DXA-based composite beam model of the proximal femur for stress estimation; Yang L, McCloskey E.V, Eastell R; Jul. 2006; Journal of Bone and Mineral Research; vol. 21, No. 7.
Does follow-up duration influence the ultrasound and DXA prediction of hip fracture? The EPIDOS prospective study; Hans D, Schott A.M, Duboeuf F, Durosier C, et al; Aug. 2004; Bone (New York); vol. 35, No. 2.
Assessment of fracture risk by bone density measurements; Jergas M, Glesser C.C; Jul. 1997; Semin Nucl Med; vol. 27, No. 3.
Femoral strength is better predicted by finite element models than QCT and DXA; Cody D.D, Gross G.J, Hou F.J, et al; Oct. 1999; Journal of Biomechanics; vol. 32, No. 10.
A mathematical model that improves the validity of osteoarthritis diagnoses obtained from a computerized diagnostic database; Gabriel S.E, Crowson C.S, O'Fallon W.M; Sep. 1996; Journal of Clinical Epidemiology; vol. 49, No. 9.
Biomedical evaluation of hip fracture using finite element model that models individual differences of femur; Harada Atsushi, Mizuno Masashi, Nakanishi Takafumi, et al; Sep. 2004; Nippon Kikai Gakki Ronbunshu A; vol. 70, No. 9.
3D reconstruction of femoral shape using a parametric model and two 2D fluoroscopic images; Kurazume R, Nakamura K, Okada T, Sato Y, et al; 2007; 2007 IEEE International Conference on Robotics and Automation; IEEE Cat No. 07CH37836D.
Analysis of ultrasound images based on local statistics, application to the diagnosis of development dysplasia of the hip; de Luis-Garcia R, Aja-Fernandez S, Cardenes-Almeida R, et al; 2007; 2007 IEEE Ultrasonics Symposium.
Subject-specific finite element models implementing a maximum principal strain criterion are able to estimate failure risk and fracture location on human femurs tested in vitro; Schileo E, Taddei F, Cristofolini L, Viceconti M; 2008; Journal of Biomechanics; vol. 41, No. 2.
Wave proppagation characteristics in long bones to diagnose osteoporosis; Chen I.I.H, Saha S; 1987; Journal of Biomechanics; vol. 20, No. 5.
Reconstruction of patient-specific 3D bone model from biplanar X-ray images and point distribution models; Zheng G; 2006 International Conference on Image Processing.
Early identification of radiographic osteoarthritis of the hip using an active shape model to quantify changes in bone morphometric features: can hip shape tell us anything about the progression of osteoarthritis?; Gregory JS, Waarsing JH, Day J, Pols HA, Reijman M, Weinans H, et al; Nov. 2007; Arthritis Rheum; 56(11).
Altman, R.D. & Gold, G.E. 2007, "Atlas of individual radiographic features in osteoarthritis, revised", Osteoarthritis and Cartilage, vol. 15, No. SU PP L. 1, pp. 1-56.
Arthritis Research Campaign. Arthritis: the big picture. 2002. Cheltenham, Arthritis Research Campaign.
Deletion of active ADAMTS5 prevents cartilage degradation in a murine model of osteoarthritis; Glasson SS, Askew R, Sheppard B, Carito B, Blanchet T, Ma HL et al; Nature 434: 644-648, 2005.
Magnetic resonance imaging (MRI) of articular cartilage in knee osteoarthritis (OA): morphological assessment; Eckstein F, Cicuttini F, Raynauld JP, Waterton JC, Peterfy C; Osteoarthritis Cartilage 14 Suppl A: A46-A 75, 2006.

(56) References Cited

OTHER PUBLICATIONS

A method for assessment of the shape of the proximal femur and its relationship to osteoporotic hip fracture; Gregory JS, Testi D, Stewart A, Undrill PE, Reid DM, Aspden RM; Osteoporos Int 15: 11, 2004.
Bone shape, structure and density as determinants of osteoporotic hip fracture: A pilot study investigating the combination of risk factors; Gregory JS, Stewart A, Undrill PE, Reid DM, Aspden RM; Invest Radiol 40: 591-597, 2005.
Osteoarthritis: a problem of growth not decay?; Aspden RM; Rheumatology 47: 1452-1460, 2008.
Osteoarthritis is a systemic disorder involving stromal cell differentiation and lipid metabolism; Aspden RM, Scheven BAA, Hutchison JD; Lancet 357: 1118-1120,2001.
High levels of fat and (n-6) fatty acids in cancellous bone in osteoarthritis; Plumb MS, Aspden RM; Lipids in Health and Disease 3: 12, 2004.
The association of lipid abnormalities with tissue pathology in human osteoarthritic articular cartilage; Lippiello L, Walsh T, Fienhold M; Metabolism 40:571-576, 1991.
Bone marrow fat in osteoarthritis assessed using Magnetic Resonance Imaging; Ahearn TS, Gregory JS, Redpath TW, Semple SIK, Hutchison JD, Knight DJ et al; Arthritis Res Ther submitted 2008.
Development of a logically derived line drawing atlas for grading knee osteoarthritis; Nagaosa Y, Mateus M, Hassan B, Lanyon P, Doherty M; Annals of the Rheumatic Diseases 59: 587-595, 2000.
Whole-organ magnetic resonance imaging score (WORMS) of the knee in osteoarthritis; Peterfy, C. G., Guermazi, A., Zaim, S., Tirman, P. F. J., Miaux, Y., White, D., et al.; 2004; Osteoarthritis and Cartilage, 12(3), 177-190.
"Substantial superiority of semiflexed (MTP) views in knee osteoarthritis: A comparative radiographic study, without fluoroscopy, of standing extended, semiflexed (MTP), and schuss views"; Buckland-Wright, J.C., Wolfe, F., Ward, R.J., Flowers, N. & Hayne, C; 1999; Journal of Rheumatology, vol. 26, No. 12, pp. 2664-2674.
Council for International Organizations of Medical Sciences & University of Manchester. Dept. Rheumatology 1963, The epidemiology of chronic rheumatism: a symposium organized by the Council for International Organizations of Medical Sciences . . . ; Kellgren, J.H. proceedings held Aug. 28-Sep. 1, 1961 J, Blackwell Scientific Publications, Oxford.
Practical statistics for medical research, 1 st edn, Chapman and Hall, London; Altrman, D.G; 1 991; New York.
"Bone marrow edema in the knee in osteoarthrosis and association with total knee arthroplasty within a three-year follow-up"; Scher, C, Craig, J. & Nelson, F.; 2008; Skeletal Radiology, vol. 37, No. 7, pp. 609-617.
Fractal analysis of trabecular bone in knee osteoarthritis (OA) is a more sensitive marker of disease status than bone mineral density (MID): Messent EA, Buckland-Wright JC, Blake GM; 2005; Calcified Tissue International, 76 (6), pp. 419-425.
Comparison of histomorphometric descriptions of bone architecture with dual-energy X-ray absorptiometry for assessing bone loss in the orchidectomized rat; Libouban H, Moreau MF, Legrand E, Audran M, Basle MF, Chappard D; 2002; Osteoporosis International ; 13 (5), pp. 422-428.
Computed tomography image analysis of the calcaneus in male osteoporosis; Cortet B, Dubois P, Boutry N, Palos G, Cotten A, Marchandise X; 2002; Osteoporosis International; 13 (1), pp. 33-41.
Bone microarchitecture and bone fragility in men: DXA and histomorphometry in humans and in the orchidectomized rat model; Audran M, Chappard D, Legrand E, Libouban H, Basle MF; 2001; Calcified Tissue International, 69 (4), pp. 214-217.
Diagnostic agreement of combined radiogrammetric analysis with texture analysis in the evaluation of bone density: A comparison with dual energy X-ray absorptiometry; Trivitayaratana W, Trivitayaratana P; 2001; Journal of the Medical Association of Thailand, 84 (suppl. 2), pp. S599-S604.
Texture analysis of X-ray radiographs is more reliable descriptor of bone loss than mineral content in a rat model of localized disuse induced by the *Clostridium botulinum* toxin; Chappard D, Chennebault A, Moreau M, Legrand E, Audran M, Basle MF; 2001; Bone, 28 (1), pp. 72-79.
Semiautomatic Segmentation of Vertebrae in Lateral X-rays Using a Conditional Shape Model; et al; Sep. 20, 2007; Academic Radiology; vol. 14, No. 10.
International Search Report of International Patent Application No. PCT/GB2009/051011.
Written Opinion of International Patent Application No. PCT/GB2009/051011.
International Search Report of International Patent Application No. PCT/GB2009/051012.
Written Opinion of International Patent Application No. PCT/GB2009/051012.
Notice of Allowance for co-pending U.S. Appl. No. 13/058,615; Form PTOL-85; 15 pages; United States Patent and Trademark Office.
Intension to Grant Notice; European Patent Office, 7 pages.

* cited by examiner

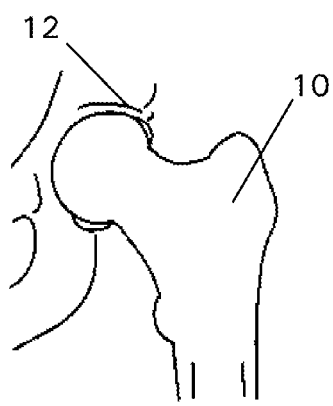
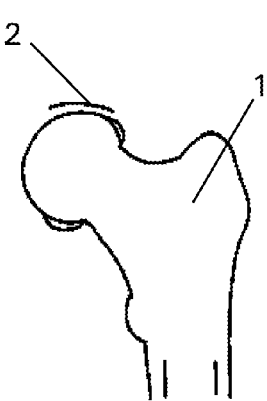
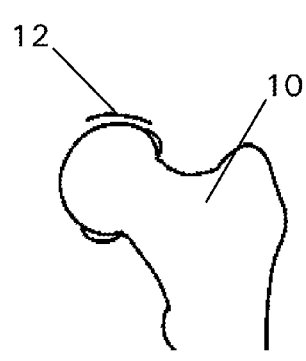
Figure 1c Figure 1b Figure 1a
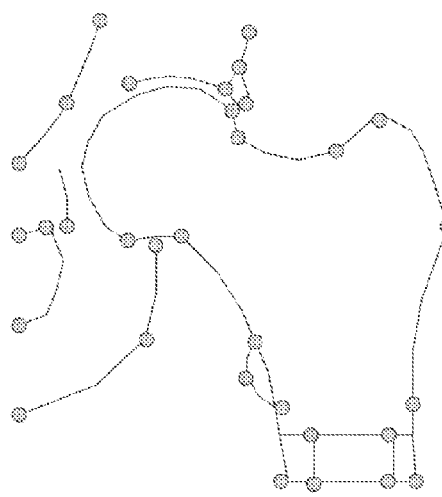
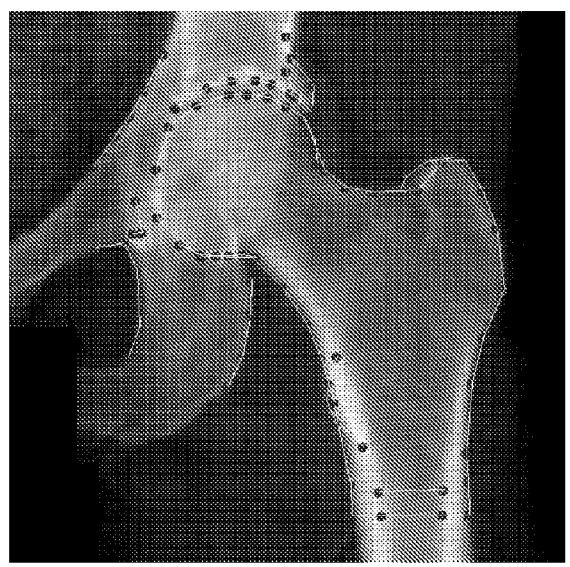
Figure 2a Figure 2b

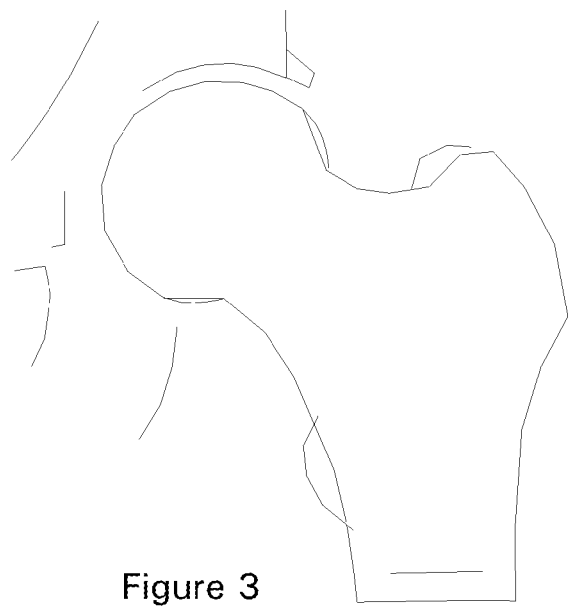
Figure 3
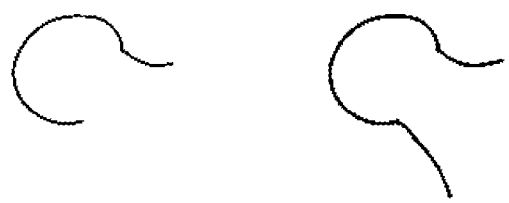
Figure 5fFigure 5e
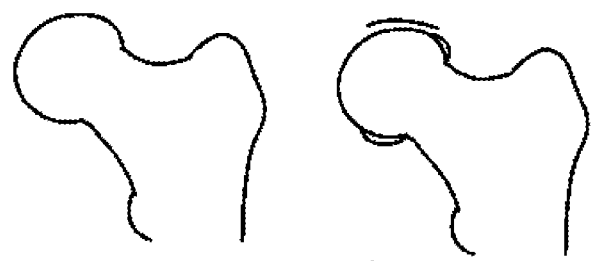
Figure 5dFigure 5c
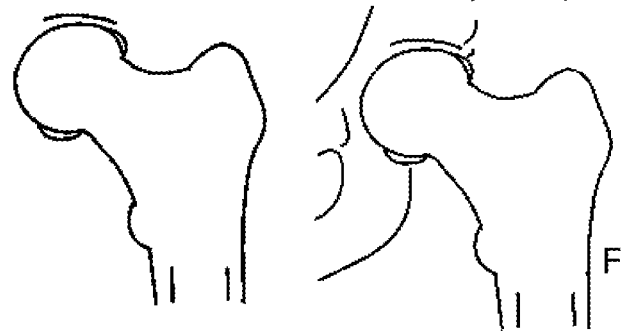
Figure 5bFigure 5a

MORPHOMETRY OF THE HUMAN HIP JOINT AND PREDICTION OF OSTEOARTHRITIS

The present invention relates to apparatus for predicting and monitoring osteoarthritis of the hip.

Osteoarthritis of the hip, or coxarthritis, affects many individuals, causing considerable pain and ultimately loss of mobility in the hip. The disease results in the breakdown of cartilage in the hip joint and the thickening of the bone. Typically, patients with advanced forms of the disease will require surgery in the form of a total hip replacement (THR), which is an invasive and costly procedure.

Although the condition currently has no cure other than hip replacement surgery, various treatments and therapies are available which aim to manage the condition and slow its progression. Typically, however, such measures are more effective if started during the early stages of the disease.

It is therefore desirable to diagnose the condition as early as possible and, ideally, to predict those at risk of developing the disease before they begin to exhibit the symptoms.

Standard clinical assessment methods for detecting the presence of osteoarthritis include geometrical analysis of bone shape based on radiographic images taken of the patient's hip. However, such methods are relatively crude, and can only provide a reliable indication of the presence of the disease at a relatively advanced stage, which means that the effectiveness of any treatment or therapy is limited.

Moreover, the rate of progression of osteoarthritis varies greatly between individuals. It would therefore be desirable to determine the severity of the disease, in terms of a predicted rate of disease progression, such as a predicted rate of progression to THR (or other surgical intervention).

Clinical imaging methods such as the Kellgren Lawrence (KL) scoring system have previously been used in research and in clinical trials for analysing the effects of osteoarthritis in various joints. For example, osteoarthritis in the knee has been quantified based on joint space width as measured from radiographic and MRI images of the knee. With such methods, images of the joint are analysed, and a score is assigned to features of the image such as joint space width, the presence of osteophytes and sub-chondral sclerosis.

However, such systems require a specially trained clinician to analyse the image. Moreover, such systems are inherently subjective, in that the results rely on the individual clinician's perception and analysis of the image. Accordingly, such methods do not lend themselves to use in routine clinical practice, and have not previously been used for this purpose.

Moreover, traditionally, such methods have rarely been used in relation to images of the hip joint for clinical assessment, as they provide little information that would affect the course of treatment, except when defining the need for surgical replacement of the joint.

As disclosed in WO 2005/045730, Active Shape Modelling techniques have been used to objectively monitor the progression of osteoporosis to predict bone fracture risk for a patient, based on Dual X-Ray Absorptiometry (DXA) images of the proximal femur. Such techniques may be used in isolation, or in combination with texture analysis of the image using Fourier transforms and Principal Component Analysis. This document also refers to the potential use of such methods for measuring the progression of osteoarthritis or Paget's disease by quantifying the deformation of the femur.

However, a more sensitive means for predicting and monitoring the onset and progression of osteoarthritis would be desirable.

It is an object of the present invention to improve on the results achievable with previously known methods and apparatus.

According to one aspect of the present invention there is provided apparatus for analysing the morphometry of a human hip joint, the apparatus comprising:— image receiving means (an image receiving module) for receiving a digital image of a hip joint;

image analysis means (an image analysis module) comprising an Active Shape Model (ASM) configured to identify a set of landmark points on said image, wherein said set of landmark points includes points which correspond to features of the proximal femur and the region of the pelvis forming the acetabulum, the ASM being further configured to generate an image data-set from the co-ordinates of said landmark points; and data comparison means (a data comparison module) for comparing said image data-set with one or more comparative data-sets to thereby obtain value(s) for one or more output modes which characterise the variation of the image data-set from the comparative data-set(s), to thereby provide an indication of the presence and/or severity of osteoarthritis in the hip and/or the risk of the hip joint developing osteoarthritis.

Although the data set generated by the ASM is dependent on location of the landmark points on the image, this data does not describe the individual anatomical features defined by the landmark points. Rather, the data set describes patterns of features in the overall joint shape.

By including features of both the acetabulum and the proximal femur in the ASM, the present inventors have found that the ASM identifies patterns in the shape of the acetabulum and the proximal femur which are linked to the presence or severity of OA in the hip, and which have not previously been associated with OA.

The apparatus of present invention is thus able to identify subtle variations in the overall shape of the joint, to thereby identify a risk of a patient developing osteoarthritis, or to identify the severity of the disease in terms of a predicted rate of disease progression, for example, a predicted rate of progression to THR or other surgical intervention.

The invention thus allows for earlier and more sensitive analysis of images of a patient's hip than previously achievable, and is even able to identify healthy patients who are at risk of developing osteoarthritis in the future. In particular, the present invention has the ability to identify individuals who are most likely to develop OA earlier than other clinical methods such as KL grade.

This enables treatment and therapy for reducing or delaying the progression of the disease to be commenced at an early stage, when it will be more effective.

The present invention is also able to provide sensitive, quantitative measures that are highly correlated with traditional clinical measures, such as KL grade, thereby avoiding the undesirable subjectivity of such measures.

Moreover, the invention can be used to predict the risk of a patient developing osteoarthritis in their hip, and/or to monitor and predict the progression of the disease, without the need for expert analysis of the image. As the need for expert analysis of the images is reduced, results can be obtained more quickly and more cost effectively than with previous methods.

The invention not only provides an imaging biomarker for identifying early stage disease and rate of progression, but may also be used as biomarker for patent stratification and monitoring OA progression in clinical trials. Clinical trials of Disease modifying Osteoarthritic Drugs (DMOADs) are estimated to take at least 10 years using previously known markers of disease, due to the scarcity of reliable markers and the consequent difficulty of identifying individuals who are at high risk of developing the disease or who have the earliest stages of the disease. DMOADS are unlikely to be effective once cartilage breakdown and changes in the bone and surrounding soft tissues are well advanced. It is thus important to identify onset of disease as early as possible. Once a DMOAD is administered, it is important to be able to compare joint changes in the treatment group with a control group over as short a time period as possible in order to assess whether the agent is effectively slowing or preventing disease progression. The previous lack of suitable markers for incidence and progression of OA means that DMOAD development is expensive and the efficacy DMOADs is difficult to establish. However, with the present invention, changes in the joint, and hence the looked-for beneficial effects of therapy, can be detected over much shorter periods of time than previously possible, and it is possible to recruit into a clinical trial those individuals best suited to test the efficacy of DMOADs, ie, those showing the earliest signs of OA (as evidenced by clinical signs such as joint pain and stiffness) and identified as having a high risk of rapid progression.

The ASM is preferably configured to identify landmark points corresponding to or defining at least the femoral head, the femoral neck and the acetabulum.

The ASM is preferably configured to identify landmark points corresponding to or defining one or more further features of the pelvis. These features may include any or all of the inner pelvic rim, the acetabular "eyebrow", the Ischial Spine, the Inferior Pubic Ramus, the Teardrop and the Obturator Foramen.

In addition, the ASM is preferably configured to identify landmark points corresponding to or defining features of any or all of the greater trochanter, the lesser trochanter, the femoral head, the femoral neck, the femoral shaft, the acetabulum, and/or the soft tissues that lie between the acetabulum and the proximal femur.

Each of the above features has been found by the inventors to add to the sensitivity of the ASM in identifying previously unrecognised patterns of features that are related to the presence and/or severity of OA. Together, these features describe the overall shape of the hip joint, how the femur sits inside the acetabulum and how it is aligned compared to the rest of the pelvis.

In certain embodiments, the ASM may be further configured to identify a set of regions defined by said landmark points on the image, to generate data representative of the image intensity within each said region and include said data in the image data set. In this case, the ASM may be described as an Active Appearance Model (AAM).

In this case, the digital image of the hip joint is preferably a Dual X-Ray Absorptiometry (DXA) image. In such images, the image intensity represents Bone Mineral Density (BMD). This enables "textural" information about the structure of the bone within the regions defined by the landmark points to be incorporated into the data set, and thus allows features such as sub-chondral sclerosis to be taken into account by the ASM.

The comparative data-set(s) may be obtained by applying the ASM to one or more images of different hip joint(s). In practice, the comparative data-sets may include the image data-set for the hip joint that is being analysed.

The comparative data sets may include data representative of the coordinates of landmark points identified in the image, and may additionally include data representative of the image intensity in regions defined by said landmark points on the image.

The comparative data-sets may be obtained from images taken for a group of subjects, which may be selected to cover the whole range from normal to abnormal hip joints.

The data comparison means is preferably configured to apply Principal Component Analysis to characterise the variation of the image data-set from the comparative data-sets in terms of independent modes of variation.

Where there is more than one comparative data-set, the data comparison means preferably compares the image data-set with the comparative data-sets by examining how the location of landmark points deviates from the mean co-ordinates of the comparative data-set(s).

For example, the image data-set under analysis may be compared with the comparative data-sets and "positioned" along the mode scores in terms of how many standard deviations it is from the mean of that mode for the whole group.

The image analysis means may comprise a plurality of ASMs for identifying different sets of landmark points on the image. These may include a master-ASM and one or more sub-ASMs, each sub-ASM being configured to identify a subset of the landmark points the master ASM is configured to identify. There may be a series of one or more sub-ASMs, the first being configured to identify a subset of the landmark points the master-ASM is configured to identify, and the further sub-ASM(s) each being configured to identify a subset of the landmark points identified by the previous sub-ASM in the series.

The digital image of the hip joint may be obtained from a radiographic image, a Dual X-ray Absorptiometry (DXA) image, a Magnetic Resonance Image (MRI), a Computed Tomography (CT) image, or an ultrasound image thereof.

In the case of a DXA image, any suitable DXA scanner may be used, as are commercially available and known in the art.

According to another aspect of the present invention there is provided a method for analysing the morphometry of a human hip joint, the method comprising:— obtaining a digital image of a hip joint;

applying to said image an Active Shape Model (ASM) configured to identify landmark points on said image, wherein said landmark points correspond to features of, at least, the proximal femur and the region of the pelvis forming the acetabulum, generating an image data-set from the co-ordinates of said landmark points; and comparing said image data-set with one or more comparative data-sets to thereby obtain value(s) for one or more output modes which characterise the variation of the image data-set from the comparative data-set(s).

The values for these output modes may be interpreted as an indication of the risk of the hip joint developing osteoarthritis and/or the severity of osteoarthritis in the hip.

According to another aspect of the present invention there is provided a computer program for analysing the morphometry of a human hip joint, the program comprising:— image receiving code for receiving a digital image of a hip joint;

image analysis code comprising Active Shape Model (ASM) code configured to identify a set of landmark points on said image, wherein said set of landmark points includes points which correspond to features of the proximal femur and the region of the pelvis forming the acetabulum, the ASM code being further configured to generate and store an image data-set from the co-ordinates of said landmark points; and data comparison code configured to compare said image data-set with one or more comparative data-sets to thereby obtain value(s) for one or more output modes which characterise the variation of the image data-set from the comparative data-set(s), to thereby provide an indication of the presence and/or severity of osteoarthritis in the hip and/or the risk of the hip joint developing osteoarthritis.

According to another aspect of the present invention there is provided a computer readable medium containing a computer program as defined above.

Again, in these aspects of the invention, the ASM may be configured to identify a set of regions defined by said landmark points on the image, to generate data representative of the image intensity in each said region and include said data in the image data set. In this case, the ASM may be described as an Active Appearance Model (AAM).

Embodiments of the present invention will now be described with reference to the accompanying drawings in which:—

FIGS. 1a to 1c show three examples of ASM for use with the present invention;

FIG. 2a illustrates the landmark points and outline defined by an 85-point ASM

FIG. 2b shows the 85-point ASM applied to a radiograph of the hip, and indicates the locations of the 85 landmark points on this image;

FIG. 3 shows the average shape determined from all images included in a study to test the 85 point ASM;

Figures 6A, 6B:
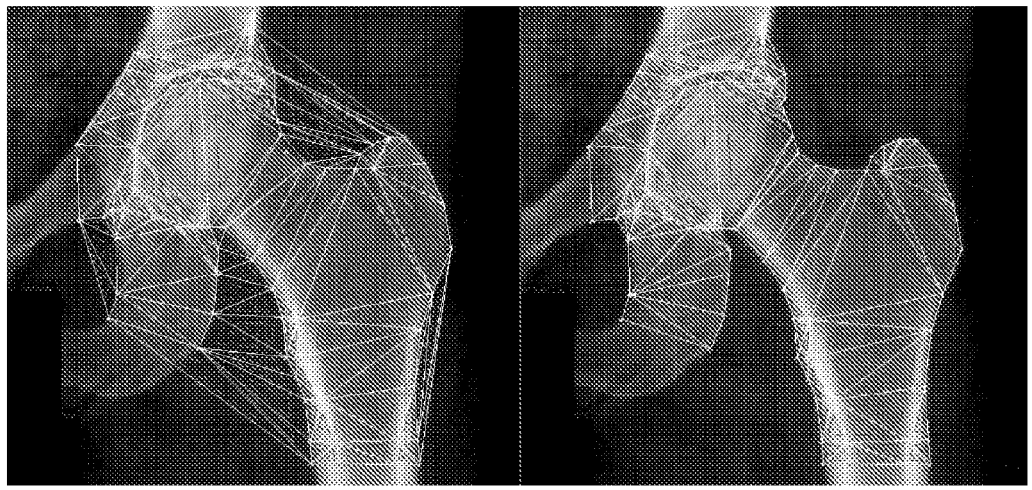

FIGS. 4a to 4e show plots of means score for modes 1, 2, 3, 4 and 7 of the 85-point ASM alongside outlines which illustrate the range of shapes for these modes;

FIGS. 5a to 5f show a master ASM and a series of five nested sub-ASMs for use with the present invention;

FIG. 6a shows triangulated regions of the 85-point ASM, as determined using the Delauney algorithm;

FIG. 6b shows the selected triangulated regions of the 85-point ASM; and

Figure 7:
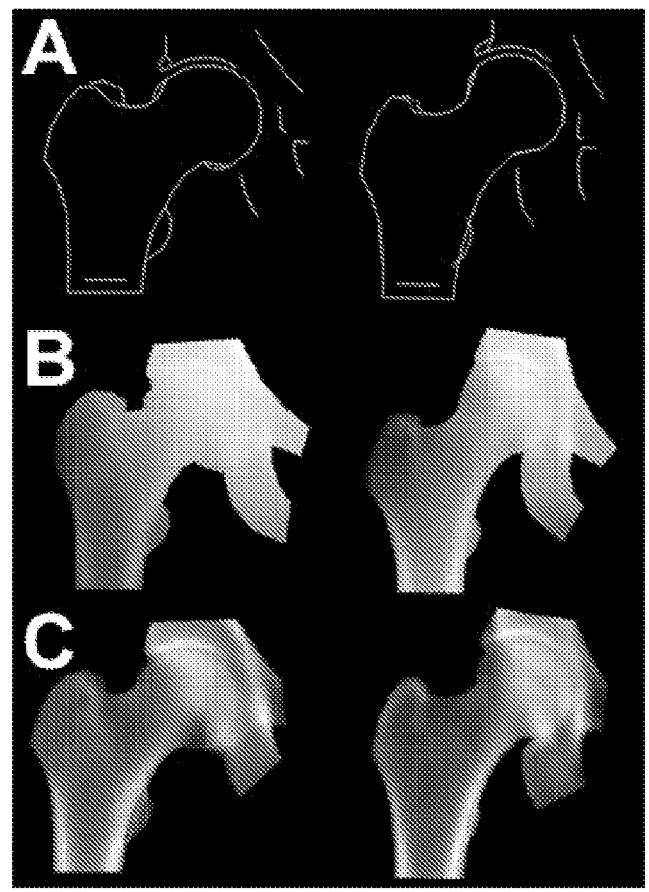

FIG. 7 shows the results of the application of an 85-point (shape only) ASM and a corresponding AAM to radiographs and DXA images.

Active Shape Modelling is an image processing technique which can be used to analyse shapes which have common features, but which are subject to natural variation.

An Active Shape Model (ASM) is a computer implemented statistical model for matching the shape of an object derived from an image or images of one or more examples of the object. The model comprises a set of landmark points, which are derived from these image(s) and identify predetermined features of the object in question. When applied to a further example of the object in a new image, the model iteratively deforms in accordance with pre-established rules to fit the example of the object in the new image. This is achieved by repeatedly searching the region surrounding each landmark point for features in the image which indicate a better location for the point, and then updating the model parameters to match the new positions, until an optimum fit to the example in the new image is found. The shape of the example in the new image can then be characterised in terms of independent modes of variation from the original shape of the model.

ASMs can thus be used to quantify differences in the shape of a body part between a patient and a control subject.

In the present case, and as discussed in more detail below, the inventors have found that an ASM which covers features of the proximal femur and parts of the pelvis, including the region of the pelvis forming the acetabulum, identifies patterns in the form of these features which have not previously been associated with OA. The inventors have found that the results can be used to indicate incipient osteoarthritis of the hip or coxarthritis, or the likelihood of a currently healthy patient developing osteoarthritis in the future, earlier than previously known clinical methods, as well as providing an objective measure of disease severity in terms of a predicted rate of disease progression.

FIGS. 1a to 1c show three examples of ASMs for use with the present invention. All three models encompass parts of the femur 10 and the pelvis 12 to build a model of the interaction of the whole joint.

In a preferred embodiment of the present invention, the apparatus comprises an 85-point ASM incorporating the proximal femur and the acetabulum. The 85-point ASM is illustrated in FIG. 1a and, in more detail, in FIG. 2. This ASM covers 85 landmark points which correspond to features observed in radiographic images of the hip joint, and identified as relevant to the onset and/or progression of osteoarthritis of the hip. In particular, the 85-point model covers features of the proximal femur, including both trochanters, the femoral head and neck and cortical thickness in the femoral shaft; parts of the pelvis including the region of the pelvis forming the acetabulum, the inner pelvic rim, the acetabular eyebrow, the Ischial Spine, the Inferior Pubic Ramus, the Teardrop and the Obturator Foramen; osteophytes; and the soft tissues that lie between the acetabulum and the proximal femur. A set of points was used to mark the tip of the greater trochanter, which has not been included in previous models of the proximal femur, due to variability in its appearance on radiographs.

The ASM is created using an active shape modelling toolkit (ASMTk) (Visual Automation Limited, Manchester, UK), a software program which runs within the MATLAB (The MathWorks Inc, Natick, USA) software environment.

To build the ASM, a set of, for example, 20 radiographic images of the hip joint are randomly selected to form a training set. The 85 landmark points are identified by an operator on each training image.

Anatomical or key points are placed at anatomical features that can be reproducibly identified on images of the hip, for example at the positions where the femoral neck meets the lesser trochanter, whilst the remaining points (secondary landmarks) are spaced at appropriate positions between these key points, for example, the evenly spaced points around the femoral head.

The software then automatically establishes a set of rules for varying the location of the landmark points to establish the optimum coordinates in a new image. In particular, the system learns to look for specific graphical features, such as hard edges or regions of relative brightness, or features having a specific form in relation to the location of each point. This can be achieved, for example, by means of the Point Distribution Model (PDM).

The apparatus further comprises a database of comparative data. The database is compiled by applying the trained ASM to a set of images taken from control subjects selected as having a healthy hip joint (ie, experiencing no symptoms of osteoarthritis in the hip joint) and osteoarthritic subjects. This ensures that the true variation observed in both healthy and diseased hip joints is included in the database and therefore encompassed within the model. The ASM iteratively deforms in accordance with the aforementioned rules to automatically determine the location of the 85 landmark points for each of the control images.

As part of this process, the software aligns the shapes in the control images by scaling, rotating and translating them in order to minimise the variance, in distance, between equivalent points. This process means that all data about the shape is stored proportionally, rather than absolutely, and the effects of the overall size of the joint on measurements are eliminated.

The co-ordinates of each landmark point for each control image is then stored in the database, together with the mean value and standard deviation for each point.

The apparatus further comprises means for receiving a digital image file containing a radiographic image of the hip region for a patient.

The radiographic image of the patient's hip is obtained using known x-ray photography means. If the image is not already in digital format, it is then scanned, or otherwise converted into a digital file, and supplied to the apparatus. The 85-point ASM is then applied to the radiographic image. The ASM iteratively deforms in accordance with the aforementioned rules to automatically determine the location of the 85 landmark points on the image of the patient's hip.

Once the model has deformed to conform to the shape of the patient's hip region, or as part of this process, the software aligns the shapes by scaling, rotating and translating them in order to minimise the variance, in distance, between equivalent points, such that the data is stored proportionally, rather than absolutely, and the effects of the overall size of the joint on measurements are eliminated. The apparatus then records the final coordinates of the landmark points to establish a data-set which characterises the morphometry of the hip joint. This data set is then compared with the comparative data stored in the database to, for example, determine the variation of the landmark points from the mean values recorded therein.

Principal Component Analysis is used to characterise the shape variation in terms of independent modes of variation. Specifically, the image is scored in terms of standard deviations of each mode from the mean for that mode.

Each mode of variation is a linear combination of the original variables (viz. the x and y co-ordinates of each landmark point) and is selected so as to be orthogonal, and therefore linearly independent, of all the other modes. When combined, the modes of variation account for 100% of the variance in the original data set, and every point contributes, to some extent, to each mode. Each mode is ordered according to the amount of variation explained. Thus, lower numbered modes account for the largest percentage of variance, whilst higher numbered modes explain little variance and can be treated as noise.

In developing the ASM of the present invention, the inventors have analysed images of the hip joint taken for healthy subjects and those suffering from osteoarthritis at various stages. Images have been obtained for a number of subjects at regular intervals over periods of up to 5 years. The presence and severity of OA for each image has then been determined in a number of ways, including analysis of the clinical symptoms at the time of the scan, the progression of these symptoms between scans, the rate of progression to THR following a scan, and by scoring the scans using KL grade.

Through this analysis, the inventors have established that several of the modes generated by an ASM which includes landmark points defining at least features of the proximal femur and the part of the pelvis forming the acetabulum, are correlated with the presence and severity of clinical symptoms of OA, the rate of progression to THR, and KL grade. In addition, the inventors have compared the results of the ASM with the results of KL scoring, and unexpectedly found that the mode scores generated by the ASM identify patterns of features and subtle variations in the overall joint shape that were not previously identifiable with KL grade, and which were not previously associated with the presence or severity of OA.

Such patterns include complex relationships between the width of the joint space, acetabular coverage and deformation of the joint caused by osteophytes, and various further aspects not previously recognised as related to osteoarthritis. For example, with the inclusion of landmark points defining at least a part of the acetabulum in the ASM, one of the modes has unexpectedly been found to identify variations in the form of the femoral head and neck, that are correlated with the progression of OA. It is thus evident that the form of the femoral head and neck, in relation to the form of the acetabulum can be used as a marker of OA.

The ASM of the invention has thus been developed to include landmark points covering at least the proximal femur and the region of the pelvis forming the acetabulum. This enables the variation of the above aspects to be quantified in terms which can be used to indicate, for example, the severity or risk of developing osteoarthritis.

In addition to identifying previously unidentified patterns of features as related to OA, the ASM of the present invention represents a more comprehensive model of the hip joint than previously known, and incorporates many more of the signs of and risk factors for osteoarthritis or coxarthritis than previously known methods. This enables a more comprehensive understanding of the whole joint and the interaction between the femur, pelvis and adjacent soft tissues than previously available.

For example, bone alignment and joint incongruity are understood to be key risk factors leading to the development of osteoarthritis, since badly aligned bones and joint incongruity can lead to osteoarthritis via bio-mechanical factors. Such factors have previously been difficult to identify and to quantify, and it has not previously been possible to reliably predict future osteoarthritis sufferers on this basis. However, the ASM used with the present invention is able to provide a measure of bone misalignment and joint incongruity, which can be used to give an indication of the likelihood of a particular patient developing the disease.

The ASM is also able to quantify cartilage degradation and bone migration, both of these factors being important indicators of the stage of the disease, and thus allow the severity of disease to be quantified.

The present invention has been described above in terms of an 85 point ASM. However, the principles of the invention would apply equally to an ASM having a different number of points, provided these cover features of the proximal femur and the region of the pelvis forming the acetabulum. For example, in another preferred embodiment of the invention, a 44-point ASM which covers features of the proximal femur and the region of the pelvis forming the acetabulum may be used. The features covered by the 44-point ASM are illustrated in FIG. 1c.

The present invention has been tested using images from the Manchester Primary Care Rheumatology Hip study. This is a five-year prospective cohort study of patients presenting to primary care with pain which their physician considered to originate from the hip. Anteroposterior pelvic radiographs were taken for a subset of 87 subjects, and radiographic severity of Osteoarthritis was assessed using the KL scoring system, this being a subjective visual assessment by a trained clinician.

The subjects were divided into two groups. The first (control) group (non-THR) included those who did not undergo a total hip replacement (THR) or show any change in KL grade during the study (n=72). The second group included those who underwent a THR during the study (n=15).

Radiographs were assessed using the 44-point ASM mentioned above. Logistic regression was used to assess the relationships between the ASM modes of variation, the KL scores and the instances of THR.

The 44-point ASM identified significant differences between the THR and non-THR groups at baseline. Two of the first 10 modes of variation identified a significant difference between the two groups at baseline (P<0.05) and two more showed a trend towards significance (P=0.06). Modes which were associated with typical osteoarthritis characteristics, such as osteophytes and joint space narrowing, were significantly correlated with the KL score, (P≤0.001). However, for mode 2, which concerns changes in the shape of the femoral head and neck, but not in joint space narrowing or osteophytes, the correlation remained significant even when adjusted to take account of the KL score (P=0.03). The shape characteristics identified in mode 2 do not relate to previously known indicators of osteoarthritis, such as joint space narrowing or progression of osteophytes, but relate to previously unidentified changes in the shape of the femur and the acetabulum.

Thus, for mode 2, the association with disease remained even after adjustment for radiographic change as assessed under the KL scoring system. This demonstrates that the ASM of the present invention provides additional information about the likelihood of progression over that available from such previously known techniques.

Moreover, the significant correlation of the other modes with the KL score indicates that the ASM could be used as an alternative to the subjective KL scoring system, to describe characteristic changes caused by osteoarthritis in a less subjective and more sensitive way.

In another test, based on 777 images from the same study, six of the first 10 modes in the 44-point ASM showed significant correlation with KL score, with the strongest correlation in modes 3 and 4 (r=−0.32 and 0.41 respectively, P<0.001). Mode 3, associated with widening and flattening of the femoral head and superior femoral head osteophyte formation, negatively correlated with KL score. A small decrease in mode score was observed in mild osteoarthritis (KL=0 and 1), whilst larger changes were seen in severe osteoarthritis (KL=3 and 4). Mode 4, which captures joint space narrowing, osteophyte formation and deformation of the femoral neck, showed nearly perfect linear relationship between the average mode 4 score in each KL grade and the KL grade itself.

Thus, certain shape model outputs (modes) from the ASM of the present invention show significant correlation with KL scores of osteoarthritis severity. The present invention thus allows for objective quantification of radiographic osteoarthritis severity based on shape, using continuous variables, which was not possible previously.

The present invention was further tested by applying the 85-point ASM discussed above to 62 individuals at baseline, and then at follow up intervals of 6 and 12 months. The average hip shape from all the images in the study (both hips, baseline and follow-up time-points) is shown in FIG. 3. All of the images were included in the ASM so that it describes the total variation in shapes present in the dataset. Accordingly, the mean shape from the ASM is effectively an outline of a hip with moderate OA. Correlations between each hip-shape mode, age and KL grade were assessed to identify modes likely to be of interest for assessing OA progression. These were then analysed using one-way ANOVAs.

Figure 4A:
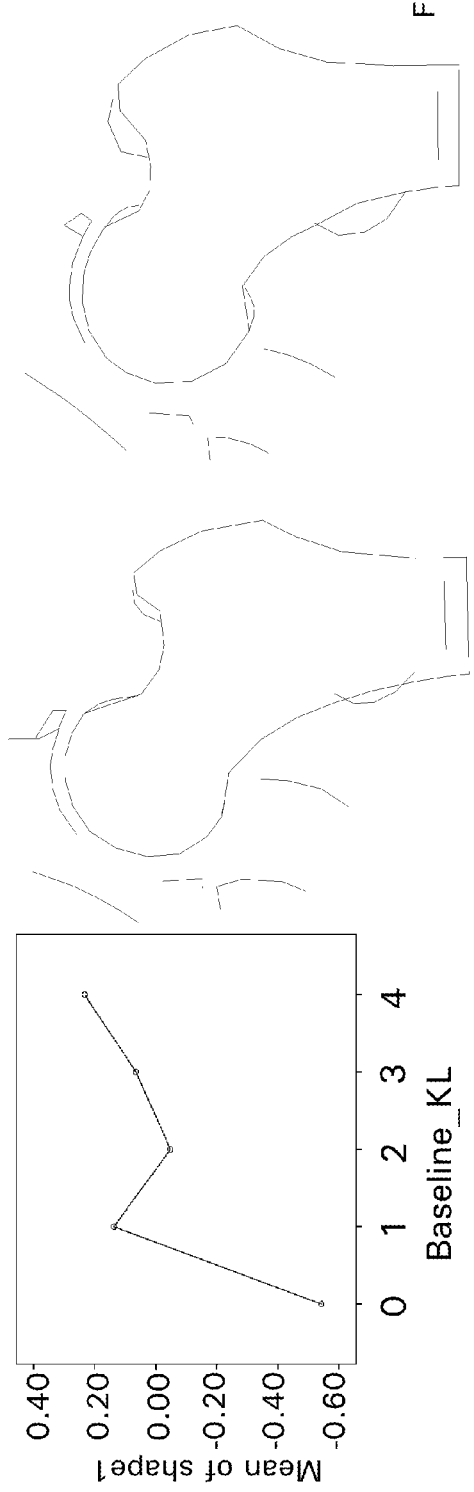

FIG. 4a shows a plot of the mean score for mode 1 at each KL grade and line drawings showing the extremes of shape variation (±3 standard deviations). ANOVA P=0.002 and correlation=0.11 (P=0.042). An increase in KL grade is significantly associated with increased mode 1 score. There is evidence of flattening of the femoral head and osteophyte formation with a high mode score (right hand drawing) although some signs of rotation/femoral anteversion are evident from the observed change in position of the lesser trochanter.

Figure 4B:
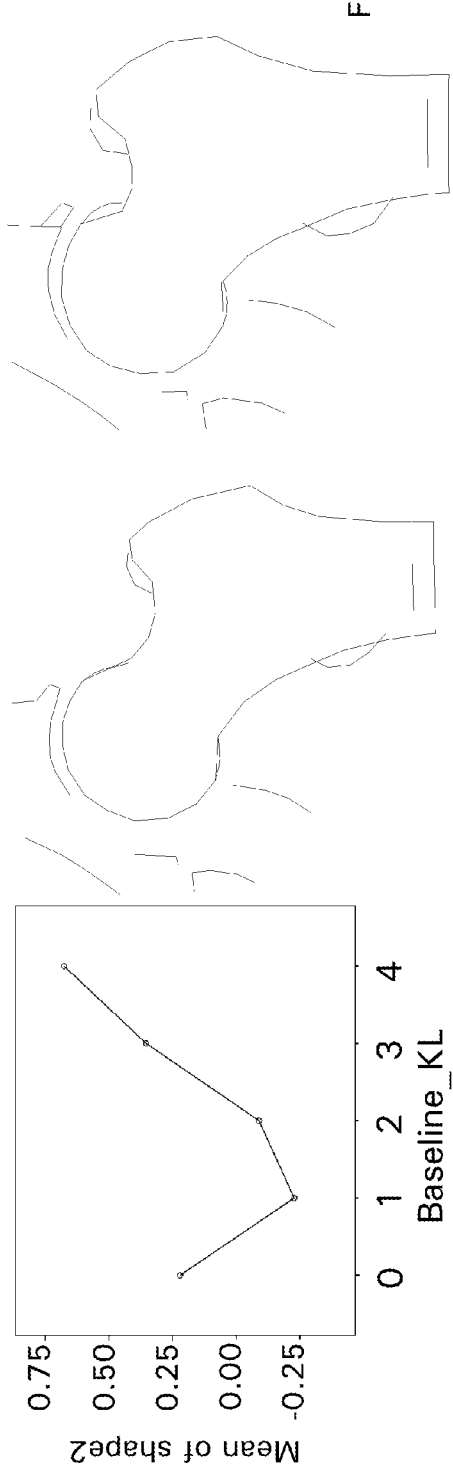

FIG. 4b shows a plot of the mean score for mode 2 at each KL grade and line drawings showing the extremes of shape variation (±3 standard deviations). ANOVA P<0.001 and correlation=0.17 (P=0.002). There is no linear association of mode 2 score and KL. However evidence of osteophytes, femoral head flattening, joint space narrowing and thickening of the femoral neck is observed with high mode score. The curvature of the superior femoral neck is much sharper in high mode 2 scores.

Figure 4C:
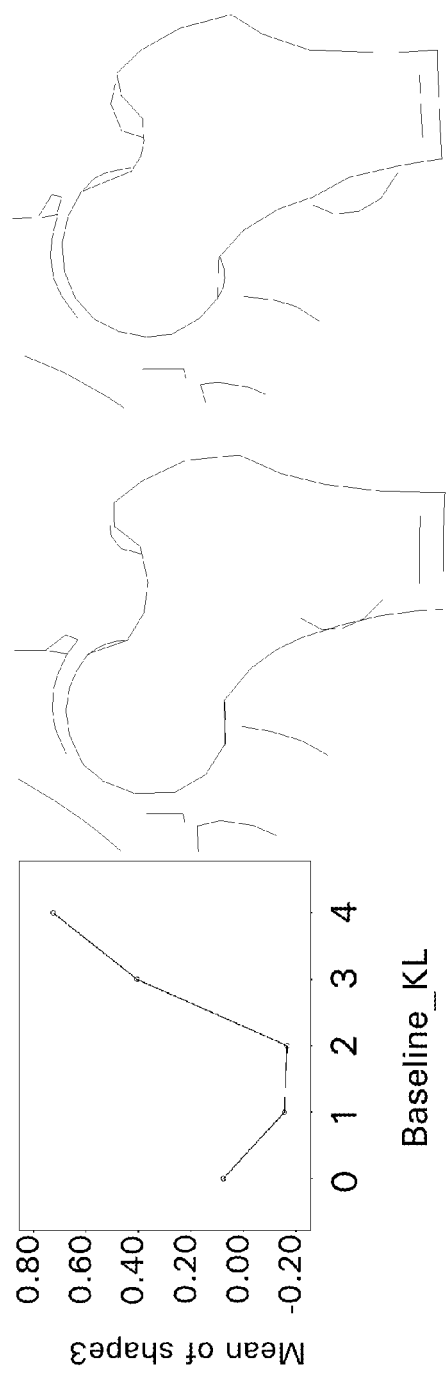

FIG. 4c shows a plot of the mean score for mode 3 at each KL grade and line drawings showing the extremes of shape variation (±3 standard deviations). ANOVA P<0.001 correlation=0.18 (P=0.001). There is no linear association of mode 3 score and KL, high mode 3 scores are seen in severe OA (grades 3 and 4). Evidence of osteophytes is observed with high mode score but rotation/femoral anteversion are evident from the observed change in position of the lesser trochanter.

Figure 4D:
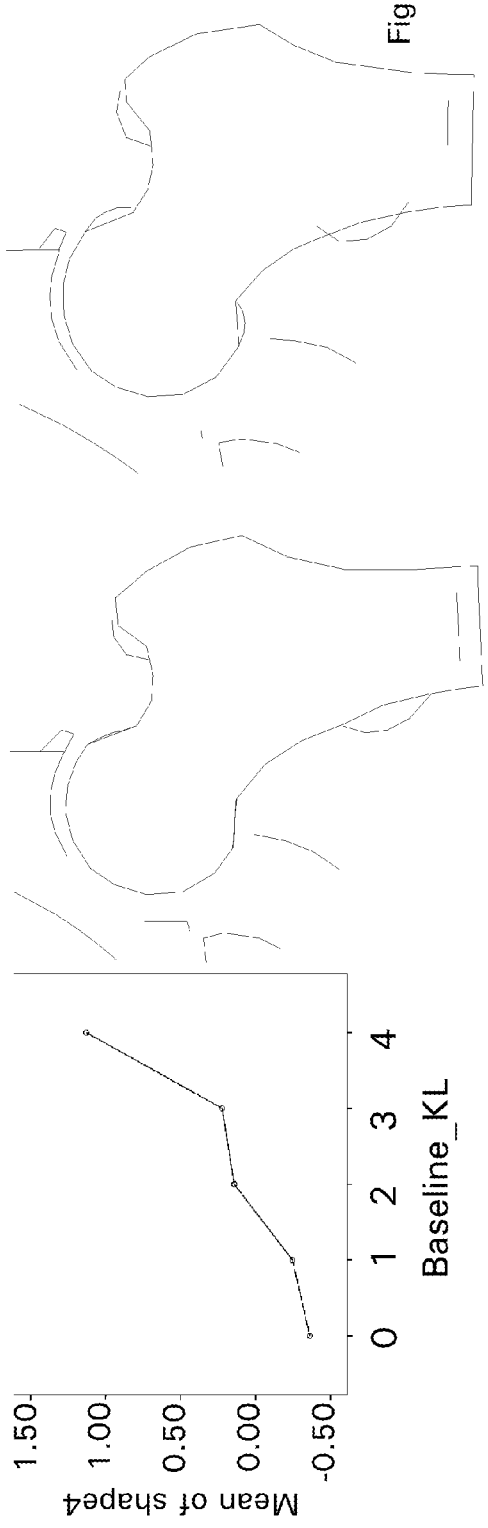

FIG. 4d shows a plot of the mean score for mode 4 at each KL grade and line drawings showing the extremes of shape variation (±3 standard deviations). ANOVA P<0.001 and correlation=0.35 (P<0.001). A monotonically increasing relationship between mode score and KL grade is observed. High mode scores are associated with osteophytes, joint space narrowing and femoral head flattening. The femoral neck appears wider, but the curvature of the superior femoral neck is similar for both extremes, unlike mode 2. Not much evidence of rotation is observed.

Figure 4E:
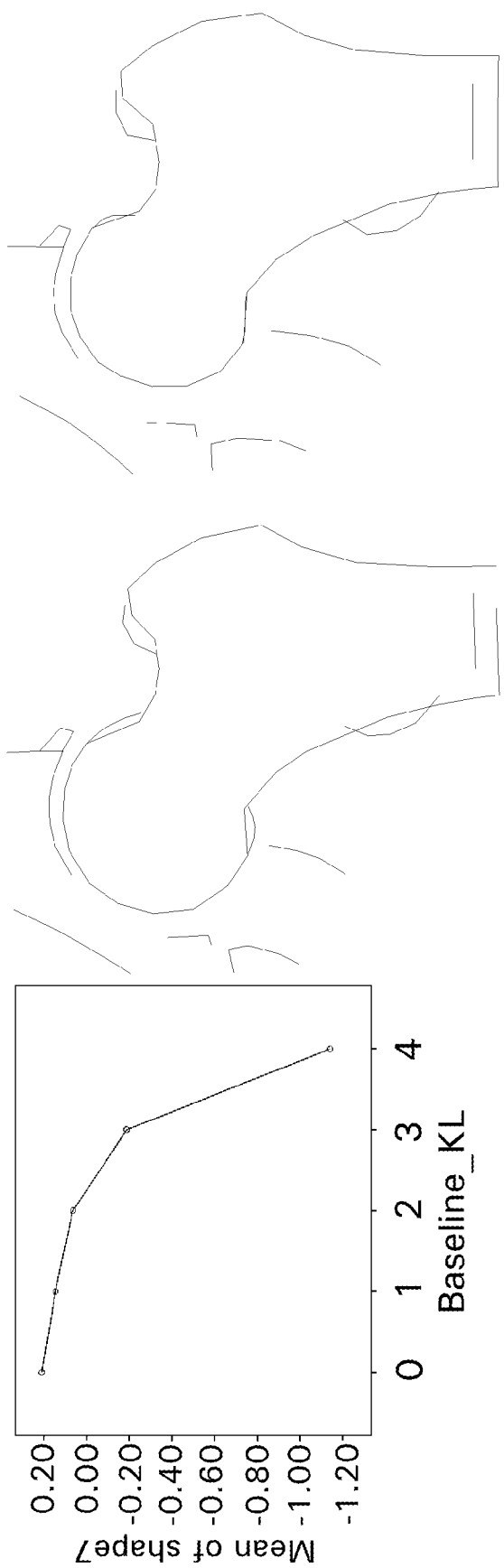

FIG. 4e shows a plot of the mean score for mode 7 at each KL grade and line drawings showing the extremes of shape variation (±3 standard deviations). ANOVA P<0.001 correlation=−0.28 (P<0.001). The mode score decreases with increasing KL grade, with the greatest change in severe OA (grades 3 and 4). Both extremes have a similar shape for the femur, with differences only evident in joint space narrowing and osteophytes, characteristics of severe OA.

Thus, several shape modes showed characteristic features of osteoarthritis. From the five modes summarized above, only one mode (mode 3) was strongly associated with internal rotation of the hip, modes 4 and 7 were associated with characteristic features of OA, such as osteophytes and joint space narrowing, whereas modes 1 and 2 were additionally associated with changes in the shape of the femoral head and neck.

These results thus show clear relationships between the shape of the hip joint and the severity of osteoarthritis. Mode scores alone provide a quantitative measure of disease and may be combined with other factors. Odds ratios may be calculated showing the risk of rapid progression to a THR. The present invention thus provides considerable benefits over traditional scoring systems for assessing disease severity and identifying rapid progressors from conventional radiographs.

In another test, clinical factors associated with OA were assessed using questionnaire data. Radiographs from 195 subjects enrolled in the Manchester Primary Care Rheumatology Study were used. A full set of clinical data was available in 105 subjects. Baseline and 5-year follow up radiographs were digitised and severity of OA was assessed by KL grade. Duration and severity of pain and its impact on physical function were derived from a self reported questionnaire. Baseline data from subjects who underwent THR during the study were compared with hip-matched (by leg) data from those who did not progress radiographically.

In total, 6 factors were tested (found previously to be clinically relevant in this population. Using total hip replacement (THR) as outcome versus non-progressors only 3 of these factors remained in the model using forward Wald statistics. These were the use of a stick, physical function and duration of pain.

One hip from each individual was selected and the 44-point ASM was applied. ASM mode scores were compared with KL grades and clinical factors using Spearman Correlation. The results are summarised in Table 1.

During the study, 27 patients underwent THR. Baseline ASM modes 3, 4, and 9 were significantly correlated with baseline KL grade, modes 6 and 13 correlated with KL at baseline and 5 years and mode 2 was correlated with KL at five year follow-up only. Baseline mode 4 scores were significantly correlated with use of a stick, mode 6 with physical function and mode 13 with duration of pain.

Modes 3 and 4 which reflect classical features of OA such as osteophytes and joint space narrowing are highly correlated with KL grade. A number of the mode scores are correlated with pain and physical function, and, therefore, contain more information than KL scores alone.

In subjects with total hip replacement matched (by leg) with those that did not progress, logistic regression was used to adjust for KL grade alone and in combination with clinical factors. In the unadjusted model, modes 3, 4 and 13 significantly predicted total hip replacement. Following adjustment for KL grade, modes 3, 4 and 13 were no longer significant. However after adjustment for KL, mode 2 reached significance, odds ratios showing a 57% reduction in risk of total hip replacement for a 1 standard deviation increase in ASM mode score. The inclusion of clinical factors in the model strengthened this finding giving a 72% reduction in risk of total hip replacement for each standard deviation increase in mode score.

In a preferred embodiment of the present invention, the ASM is a nested ASM. That is to say, the ASM comprises a "master ASM" including the total set of landmark points covering the whole hip joint, from which nested sub-models can be automatically extracted.

The present inventors have established that such a nested ASM can provide a standardised method of assessment and enable individual features and correlations between features to be identified.

In the present embodiment, the master ASM is the 85-point ASM, illustrated in FIGS. 1a and 2, and includes the proximal femur, parts of the pelvis, including the acetabulum, osteophytes and cortical width in the femoral shaft. There are then a series of five nested sub-models, each comprising successive sub-sets of the 85 landmark points. That is to say, each sub-model in the series comprises a sub-set of the points covered by the previous model in the series.

The regions covered by the nested ASM are illustrated in FIGS. 5a to 5f. FIG. 5a illustrates the features covered by the master ASM, whilst FIG. 5b covers the features covered by the first sub-model, and so on. FIG. 5f shows the features covered by a sub-model, which comprises 16 landmark points covering the femoral head and neck. As can be seen, the master ASM and the first two sub-models cover features of the proximal femur and the pelvis, whilst the smaller sub-models cover only the proximal femur.

In alternative embodiments of the invention, different sub-models covering different sub-sets of points may be developed. In particular, each sub-model may comprise any sub-set of points from the master ASM.

The nested ASM of the present embodiment was applied to 777 images of hips from 193 subjects from the Manchester Primary Care Rheumatology Study.

Similarities between modes in the different ASM designs were assessed by both visual inspection of the shape variation characterized by each mode and statistically, using Pearson's correlation.

Close links were found between different ASM designs. The advantages of the nested ASM are evident in that relationships between features of osteoarthritis can be explored.

The smaller ASMs, including the 16-point ASM of FIG. 5f which covers features of the proximal femur examine shape variation in a selected area, whilst the bigger ASMs provide a more comprehensive view of the joint.

For example, 'flattening' of the femoral head, was clearly characterized by mode 1 in the 16-point model of FIG. 5f, but was associated with 2 or more modes in the larger models. The larger ASMs, however, enabled this to be correlated with other features such as osteophytes, changes in femoral neck width or neck shaft angle and joint space width.

The nested-ASM thus provides a simple and effective means for assessing OA and, when employed universally using the same set of points, enables direct comparison between studies using different model designs.

Active Shape Models use sets of points to identify the outline of the bones and landmark points are placed on defined anatomical features. The precision of the model is maximized by using mathematical constraints to ensure precise and even spacing of intermediate points along smooth lines between landmarks, such as over the femoral head. By using the same set of points, differences between studies will be due to differences in study group, rather than inter-observer variation. Large ASM templates allow visualization of the whole hip joint, whilst smaller models highlight variation in selected regions. Nested designs enable measurement of changes in shape, and their association with OA at all these different levels.

The application of the ASM of the invention to general radiographic images is described above. However, the principles of the present invention may equally be applied with other types of image. For example, an ultrasound, Computed Tomography (CT) or MRI image.

In particular, the ASM may be applied to images obtained through Dual X-ray Absorptiometry (DXA) scans. DXA scans use two energies of x-ray beams to calculate Bone Mineral Density (BMD). Modern DXA scanners acquire high resolution images allowing possible visualisation of traditional radiographic osteoarthritis features including joint space narrowing and osteophytes, in addition to BMD, whilst exposing the patient to a much lower radiation dose.

The present inventors have established that DXA images can be used to grade severity of osteoarthritis using a standard radiographic scoring method, the Kellgren Lawrence (KL) system, and that the relationship between the shape of the femur and the severity of osteoarthritis observed in radiographs is also found with DXA images using the ASM of the present invention.

Subjects were recruited using the local Radiology Information System. In total 62 subjects, identified as having had a pelvic radiograph in the last 12 months, were invited to undergo a DXA scan of both femurs using an iDXA scanner (GE Medical Systems). Using the DXA images, each hip was graded using the KL system. In a subset of 11 subjects (22 hips) both DXA images and matched radiographs were graded by 3 observers at least 1 week apart.

A 44-point ASM covering the femoral head and superior femoral neck, both trochanters, part of the acetabulum and osteophytes, was applied to all DXA images. Pearson correlation was used to test the relationship of the results of the ASM with the KL score.

Good intra-observer repeatability was found for KL scoring based on the DXA images (Quadratic weighted Kappa 0.83-0.87). Similarly good intra-observer repeatability was found, for KL scoring, between the DXA and radiograph images (Quadratic weighted Kappa 0.63-0.87). This indicates that the radiographic appearance of osteoarthritis is comparable on both radiographic and DXA images.

Two of the first 10 modes from the 44-point ASM (modes 1 and 6) were significantly associated with an increased KL score (P<0.0001), with greater correlation coefficients than the 16-point model (r=0.37, compared to 0.28).

These results show that both KL scoring and ASM models for grading the severity of OA can be applied to DXA scans, opening the possibility of radiographic assessment of the disease using a lower radiation dose and simultaneously gathering data on BMD.

In another preferred embodiment of the present invention, the ASM is an Active Appearance Model (AAM).

An AAM is a computer implemented algorithm for matching a statistical model of object shape and appearance to another example of the object in a new image. The term "appearance" in this context refers to the variation of image intensity or texture. In this respect, an AAM uses an ASM to define a region of interest, and then analyses the variation of image intensity within that region. The shape and appearance of the example in the new image can then be characterised in terms of linearly independent modes of variation from the original shape and appearance of the model. AAMs can thus be used to quantify differences in the shape and appearance of a body part between a patient and a control subject.

An AAM is built in the same way as an ASM, using a set of landmark points to describe the outline of one or more features of the object as it appears in an image. In addition to describing the shape, the landmark points are used to segment each feature into a set of triangular regions, with a landmark point at each vertex of each triangle. Appearance (or texture) modes of variation, which quantify the distribution and intensity of the pixels within each region can then be calculated as well as shape modes of variation using Principal Component Analysis. Linear combinations of the shape and appearance modes of variation may then be determined.

Although AAMs may be applied to radiographs, the inventors have established that it is preferable to use images generated from DXA scan data, as the image intensity is standardised in such images. Although DXA images have lower resolution than radiographs, they are acquired using a lower radiation dose and have the added advantage that the image intensity reflects bone mineral density (BMD), such that an AAM applied to a DXA image can describe not only features of the shape of the hip joint, but also the internal, spatial distribution of BMD. An AAM applied to a DXA scan thus include data representative of the distribution and variation in BMD within the shape as a series of linearly independent mode scores.

In a preferred embodiment of the invention, the AAM comprises the 85 point ASM shown in FIGS. 1a and 2 which incorporates the outline of the proximal femur, parts of the pelvis, and including osteophytes. The AAM is created using an active appearance modelling toolkit (Manchester University, Manchester, UK).

To build the AAM, a set of, for example, 20 DXA images of the hip joint are randomly selected to form a training set. The 85 landmark points are identified by an operator on each training image.

A triangulation algorithm, such as the Delauney algorithm, is then applied using the software, to automatically identify triangular regions within the model, whose corners correspond to the landmark points, as illustrated in FIG. 6a. Of these regions, the specific regions are selected, to ensure that the model covers only areas of bone, and not soft tissue, as shown in FIG. 6b.

The software then automatically establishes a set of rules for varying the location of the landmark points to establish the optimum coordinates. In particular, the system learns to look for specific graphical features, such as hard edges or regions of relative brightness, or features having a specific form in relation to the location of each point, and specific textural features in the triangular regions defined by the location of the landmark points. This can be achieved, for example, by means of the Point Distribution Model (PDM).

The apparatus further comprises a database of comparative data, which is compiled by applying the trained AAM to a set of DXA images taken from control subjects selected as having a healthy hip joint and osteoarthritic subjects. The AAM iteratively deforms in accordance with the aforementioned rules to automatically determine the location of the 85 landmark points, and thus the location of the corresponding triangular regions for each of the control images.

As part of this process, the software aligns the shapes in the control images by scaling, rotating and translating them in order to minimise the variance, in distance, between equivalent points. This process means that all data about the shape is stored proportionally, rather than absolutely, and the effects of the overall size of the joint on measurements are eliminated.

The coordinates of each landmark point for each control image is then stored in the database, together with the mean value and standard deviation for each point. The image intensity within each of the triangular regions is also stored in the database, together with the mean value and standard deviation for each region.

The apparatus further comprises means for receiving a digital image file containing a DXA image of the hip region for a patient. The DXA image of the patient's hip is obtained using known DXA imaging means, such as the GE Lunar iDXA scanner, and supplied as a digital file to the apparatus. The AAM is then applied to the DXA image. The AAM iteratively deforms in accordance with the aforementioned rules to automatically determine the location of the 85 landmark points and the corresponding triangular regions on the image of the patient's hip.

Once the model has deformed to conform to the shape of the patient's hip region, or as part of this process, the software aligns the shapes by scaling, rotating and translating them in order to minimise the variance, in distance, between equivalent points, such that the data is stored proportionally, rather than absolutely, and the effects of the overall size of the joint on measurements are eliminated. The apparatus then records the final coordinates of the landmark points, and the variation of image intensity within the triangular regions of the image, to establish a data-set which characterises the shape and appearance of the hip joint. This data set is then compared with the comparative data stored in the database to, for example, determine the variation of the landmark points from the mean values recorded therein.

Principal Component Analysis is used to characterise the shape and image intensity variation in terms of independent modes of variation, these being indicative of incipient osteoarthritis, the severity of the disease, and/or the likelihood of developing the disease at some time in the future.

Specifically, the image is scored in terms of standard deviations of each mode from the mean for that mode.

The shape and appearance of the body part may be characterised in terms of shape modes of variation, appearance modes of variation, or a linear combination of both.

Each mode of variation is a linear combination of the original variables and is selected so as to be orthogonal, and therefore linearly independent, of all the other modes. When combined, the modes of variation account for 100% of the variance in the original data set. Each mode is ordered according to the amount of variation explained. Thus, lower numbered modes account for the largest percentage of variance, whilst higher numbered modes explain little variance and can be treated as noise.

In addition to the aspects of the shape of the hip joint discussed above in relation to the 85 point shape only ASM, the 85 point AAM is able to identify areas of sclerosis in both the acetabulum and the femoral head.

Although the AAM described above has 85 landmark points, AAMs used with the present invention can contain different numbers of points, provided these cover features of the proximal femur and the region of the pelvis forming the acetabulum. Nested AAMs are also possible.

The present invention has been tested using baseline hip DXA images obtained using the GE Lunar iDXA scanner for 62 patients who had had standard radiographs of both hips taken in the preceding 12 months. The radiographs were graded using the KL scoring system. 20 patients were graded as having mild OA (KL grade of 0 or 1), 20 were graded as having moderate OA (KL grade of 2 in at least one hip) and 22 were graded as having severe OA (KL grade of 3 or 4 in at least one hip).

A model template consisting of 85 points describing the outline of the proximal femur, parts of the pelvis, and osteophytes was developed. An AAM and a (shape only) ASM were built as described above by applying the template to both the radiographs and the DXA images.

The results for the first mode are shown in FIG. 7, in which each row shows ±2 standard deviations from the means image shape for:—A) the shape only ASM applied to radiographs; B) the AAM applied to radiographs; and C) the AAM applied to DXA images.

Effective (shape only) ASMs could be built from either DXA or the radiographic images, as changes in the shape of the hip joint were clearly evident in both. However, comparison of the AAMs applied to the radiographic and DXA images showed that DXA images were more useful for AAM than radiographs, where little textural detail can be seen. The DXA-AAM clearly showed variation in bone structure, particularly between the femoral head and the acetabulum, and within the femoral neck.

From this test, it can be concluded that (shape only) ASMs are suitable for both DXA and radiographic images, although the latter may be preferable due to the higher resolution. AAMs are, however, most suitable for use in DXA images, as the image intensity is standardised.

In another test, DXA images were obtained at baseline, 6 months and 12 months for the same group of 62 patients using the GE Lunar iDXA scanner, and the 85-point AAM was applied to those images. Shape or appearance modes of interest were identified when the mean mode score monotonically increased or decreased significantly with KL grade, assessed using one way ANOVA (Analysis of Variance). These were tested for significant changes over time and with baseline radiographic KL grade using 2-way repeated measures ANOVA where images were available from all three pelvic DXA visits (54 patients).

Shape mode 4 significantly increased with increasing KL grade ($P<0.001$). It captured osteophytes, joint space narrowing and widening of the femoral head and neck. Two-way repeated ANOVA revealed significant changes over time ($P<0.00001$), with no interaction effect ($P=0.64$). Post hoc analysis showed significant differences within baseline KL grade 1 and 2. Similarly, the mean score of Appearance mode 4 significantly increased with increasing KL grade ($P<0.00001$), where higher scores were visually associated with sclerosis, joint space narrowing, widening of the femoral neck and reduced curvature of the superior femoral neck. Two-way repeated measures ANOVA revealed significant changes over time ($P<0.00001$), with no interaction effect ($P=0.12$). Post hoc analysis showed significant differences within KL baseline grades of 2 and 4.

From this test it can be concluded that changes in shape and appearance could be measured from DXA images taken 6 months apart in this one-year prospective cohort study. These results show that the shape and appearance models are sensitive enough to quantify small structural changes not matched by a change in KL grade, with certain shape and appearance modes indicating the ability to detect changes even in the mildest OA group. Shape and Appearance Modelling can thus be seen to have the power to facilitate therapeutic trials both by detecting early OA and by enabling structural progression to be monitored over short time periods.

The present inventors have found appearance modes represent a stronger classifier of OA that shape modes, and that a linear combination of shape and appearance modes is a stronger classifier of OA than either shape or appearance alone.

In the above described embodiments, the present invention has been described in terms of a method and apparatus for identifying the presence and/or severity of OA for a particular patient. However, the apparatus may also be used as biomarker for patent stratification and monitoring OA progression in clinical trials of Disease modifying Osteoarthritic Drugs (DMOADs). In this case, images may be taken for a group of selected subjects, which are analysed using the ASM/AAM to generate a data-set for each image. The results for each image may then be compared to the mean results obtained for the group (or a selection of the group) as a whole.

The invention claimed is:

1. Apparatus for analyzing the morphometry of a human hip joint, the apparatus comprising:—
    image receiving means for receiving a digital image of a hip joint;
    image analysis means comprising an Active Shape Model (ASM) configured to identify a set of landmark points on said image, wherein said set of landmark points includes points which correspond to features of the proximal femur and points which correspond to features of the region of the pelvis forming the acetabulum, the ASM being further configured to generate an image data-set from the co-ordinates of said landmark points; and
    data comparison means for comparing said image data-set with one or more comparative data-sets to thereby obtain at least one valve for one or more output modes which characterize the variation of the image data-set from the one or more comparative data-sets, to thereby provide a measure of at least one of the severity of osteoarthritis in the hip and the risk of the hip joint developing osteoarthritis.

2. Apparatus as claimed in claim 1 wherein the ASM is configured to identify landmark points corresponding to at least the femoral head, the femoral neck and the acetabulum.

3. Apparatus as claimed in claim 1 wherein the ASM is configured to identify landmark points corresponding to one or more further features of the pelvis.

4. Apparatus as claimed in claim 3 wherein the one or more further features of the pelvis includes any or all of the inner pelvic rim, the acetabular "eyebrow", the Ischial Spine, the Inferior Pubic Ramus, the Teardrop and the Obturator Foramen.

5. Apparatus as claimed in claim 1 wherein the ASM is configured to identify landmark points corresponding to features of the greater trochanter.

6. Apparatus as claimed in claim 1 wherein the ASM is configured to identify landmark points corresponding to features of the lesser trochanter.

7. Apparatus as claimed in claim 1 wherein the ASM is configured to identify landmark points corresponding to features of the femoral shaft.

8. Apparatus as claimed in claim 1 wherein the ASM is configured to identify landmark points corresponding to features of the soft tissues that lie between the acetabulum and the proximal femur.

9. Apparatus as claimed in claim 1 wherein the ASM is further configured to identify a set of regions defined by said landmark points on the image, to generate data representative of the image intensity within each said region and include said data in the image data set.

10. Apparatus as claimed in claim 9 wherein the ASM is an Active Appearance Model (AAM).

11. Apparatus according to claim 1 wherein the data comparison means is configured to apply Principal Component Analysis to characterize the variation of the image data-set from the comparative data-sets in terms of independent modes of variation.

12. Apparatus according to claim 1 wherein the data comparison means compares the image data set with the comparative data sets by examining how the location of landmark points deviates from the mean co-ordinates of the one or more comparative data-sets.

13. Apparatus according to claim 1 wherein the image analysis means comprises a plurality of ASMs for identifying different sets of landmark points on the image.

14. Apparatus according to claim 1 wherein the image analysis means comprises a master-ASM and one or more sub-ASMs, each sub-ASM being configured to identify a subset of the landmark points the master ASM is configured to identify.

15. Apparatus according to claim 14, comprising a series of one or more sub-ASMs, the first being configured to identify a subset of the landmark points the master-ASM is configured to identify, and the further one or more sub-ASMs each being configured to identify a subset of the landmark points identified by the previous sub-ASM in the series.

16. Apparatus according to claim 1 wherein the digital image of the hip joint is obtained from one of a radiographic image a Dual X-ray Absorptiometry (DXA) image, an ultrasound image, a Magnetic Resonance Image (MRI) and a Computed Tomography (CT) image thereof.

17. A method for analyzing the morphometry of a human hip joint, the method comprising:—
providing a digital image of a hip joint;
applying to said image an Active Shape Model (ASM) configured to identify landmark points on said image, wherein said landmark points correspond to features of, at least, the proximal femur and the region of the pelvis forming the acetabulum,
generating an image data-set from the co-ordinates of said landmark points; and
comparing said image data-set with one or more comparative data-sets to thereby obtain at least one value for one or more output modes which characterize the variation of the image data-set from the one or more comparative data-sets, to thereby provide a measure of at least one of the severity of osteoarthritis in the hip and the risk of the hip joint developing osteoarthritis.

18. A non-transitory computer-readable medium containing a computer program for analyzing the morphometry of a human hip joint, the program comprising:
image receiving code for receiving a digital image of a hip joint;
image analysis code comprising Active Shape Model (ASM) code configured to identify a set of landmark points on said image, wherein said set of landmark points includes points which correspond to features of the proximal femur and points which correspond to features of the region of the pelvis forming the acetabulum, the ASM code being further configured to generate and store an image data-set from the co-ordinates of said landmark points; and
data comparison code configured to compare said image data-set with one or more comparative data-sets to thereby obtain at least one value for one or more output modes which characterize the variation of the image data-set from the one or more comparative data-sets, to thereby provide a measure of at least one of the severity of osteoarthritis in the hip and the risk of the hip joint developing osteoarthritis.

* * * * *